US00PP19359P2

(12) United States Plant Patent
Dümmen

(10) Patent No.: US PP19,359 P2
(45) Date of Patent: Oct. 21, 2008

(54) ***GERANIUM* PLANT NAMED 'DUEIMLYK'**

(50) Latin Name: *Pelargonium×hortorum*
Varietal Denomination: Dueimlyk

(75) Inventor: Tobias Dümmen, Rheinberg (DE)

(73) Assignee: Capitol Green Investments Ltd., Grand Cayman (KY)

( * ) Notice: Subject to any disclaimer, the term of this patent is extended or adjusted under 35 U.S.C. 154(b) by 0 days.

(21) Appl. No.: 11/804,351

(22) Filed: May 17, 2007

(51) Int. Cl.
*A01H 5/00* (2006.01)

(52) U.S. Cl. ..... Plt./329

(58) Field of Classification Search ..... Plt./329
See application file for complete search history.

*Primary Examiner*—Anne Marie Grunberg
*Assistant Examiner*—Louanne C Krawczewicz My
(74) *Attorney, Agent, or Firm*—C. A. Whealy

(57) ABSTRACT

A new and distinct cultivar of Zonal *Geranium* plant named 'Dueimlyk', characterized by its compact and upright to outwardly spreading plant habit; freely basal branching habit; dark green-colored leaves; freely flowering habit; semi-double red purple-colored flowers; and good garden performance.

1 Drawing Sheet

Botanical designation: *Pelargonium×hortorum.*
Cultivar denomination: 'Dueimlyk'.

BACKGROUND OF THE INVENTION

The present invention relates to a new and distinct cultivar of Zonal *Geranium*, botanically known as *Pelargonium×hortorum,* and hereinafter referred to by the name 'Dueimlyk'.

The new Zonal *Geranium* is a product of a planned breeding program conducted by the Inventor in Rheinberg, Germany. The objective of the breeding program is to create new uniform Zonal *Geranium* cultivars with numerous and attractive flowers.

The new Zonal *Geranium* originated from a cross-pollination made by the Inventor in August, 2002 in Rheinberg, Germany of a proprietary selection of *Pelargonium×hortorum* identified as code number F-13-08, not patented, as the female, or seed, parent with a proprietary selection of *Pelargonium×hortorum* identified as code number E01-26, not patented, as the male, or pollen, parent. The cultivar Dueimlyk was discovered and selected by the Inventor as a flowering plant from within the progeny of the stated cross-pollination in a controlled environment in Rheinberg, Germany in May, 2003.

Asexual reproduction of the new Zonal *Geranium* by vegetative terminal cuttings in a controlled environment in Rheinberg, Germany since July, 2003, has shown that the unique features of this new Zonal *Geranium* are stable and reproduced true to type in successive generations.

SUMMARY OF THE INVENTION

The cultivar Dueimlyk has not been observed under all possible environmental conditions. The phenotype may vary somewhat with variations in environment and cultural practices such as temperature, daylength and light intensity without, however, any variance in genotype.

The following traits have been repeatedly observed and are determined to be the unique characteristics of 'Dueimlyk'. These characteristics in combination distinguish 'Dueimlyk' as a new and distinct cultivar of Zonal *Geranium:*

1. Compact and upright to outwardly spreading plant habit.
2. Freely basal branching habit.
3. Dark green-colored leaves.
4. Freely flowering habit.
5. Semi-double red purple-colored flowers.
6. Good garden performance.

Plants of the new Zonal *Geranium* differ primarily from plants of the female parent selection in flower color as plants of the female parent selection have cherry red-colored flowers.

Plants of the new Zonal *Geranium* differ primarily from plants of the male parent selection in flower color as plants of the male parent selection have deeper red purple-colored flowers.

Plants of the new Zonal *Geranium* can be compared to plants of the *Pelargonium×hortorum* cultivar Duevalent, disclosed in U.S. Plant Pat. No. 13,201. In side-by-side comparisons conducted in Rheinberg, Germany, plants of the new Zonal *Geranium* differed from plants of the cultivar Duevalent in the following characteristics:

1. Plants of the new Zonal *Geranium* were more vigorous than plants of the cultivar Duevalent.
2. Plants of the new Zonal *Geranium* had larger leaves and longer petioles than plants of the cultivar Duevalent.
3. Plants of the new Zonal *Geranium* had fewer flowers per umbel than plants of the cultivar Duevalent.
4. Plants of the new Zonal *Geranium* and cultivar Duevalent differed slightly in flower color.

BRIEF DESCRIPTION OF THE PHOTOGRAPH

The accompanying colored photograph illustrates the overall appearance of the new Zonal *Geranium*, showing the colors as true as it is reasonably possible to obtain in colored reproductions of this type. Colors in the photograph may differ slightly from the color values cited in the detailed botanical description which accurately describe the colors of the new Zonal *Geranium*. The photograph comprises a side perspective view of a typical flowering plant of 'Dueimlyk' grown in a container.

DETAILED BOTANICAL DESCRIPTION

The aforementioned photograph and following observations, measurements and values describe plants grown in Rheinberg, Germany in a glass-covered greenhouse during the summer and under conditions which closely approximate commercial production. During the production of the plants, day and night temperatures averaged 18° C. and light levels averaged 4,500 lux. Plants were about two months from planting when the photographs and the description were taken. In the detailed description, color references are made to The Royal Horticultural Society Colour Chart, 2001 Edition, except where general terms of ordinary dictionary significance are used.

Botanical classification: *Pelargonium×hortorum* cultivar Dueimlyk.

Parentage:

*Female, or seed, parent.*—Proprietary selection of *Pelargonium×hortorum* identified as code number F-13-08, not patented.

*Male or pollen parent.*—Proprietary selection of *Pelargonium×hortorum* identified as code number E01-26, not patented.

Propagation:

*Type.*—By vegetative terminal cuttings.

*Time to initiate roots, summer.*—About five days at temperatures of 20° C.

*Time to initiate roots, winter.*—About seven days at temperatures of 20° C.

*Time to produce a rooted young plant, summer.*—About three weeks at temperatures of 20° C.

*Time to produce a rooted young plant, winter.*—About four weeks at temperatures of 20° C.

*Root description.*—Fine, fibrous; white in color.

*Rooting habit.*—Freely branching.

Plant description:

*General appearance.*—Compact and upright to outwardly spreading plant habit; uniformly rounded; densely foliated.

*Growth and branching habit.*—Moderately vigorous growth habit. Freely basal branching habit with about three lateral branches developing per plant.

*Plant height, to top of umbels.*—About 20 cm.

*Plant height, to top of foliar plane.*—About 10 cm.

*Plant width.*—About 23 cm.

*Lateral branches.*—Length: About 5.5 cm. Diameter: About 2 mm to 5 mm. Internode length: About 9 mm. Texture: Slightly pubescent. Strength: Strong. Color: 144A.

Foliage description:

*Arrangement.*—Alternate; simple.

*Length.*—About 7.4 cm.

*Width.*—About 8.8 cm.

*Shape.*—Reniform.

*Apex.*—Rounded.

*Base.*—Cordate.

*Margin.*—Crenate.

*Venation pattern.*—Palmate.

*Texture, upper and lower surfaces.*—Pubescent.

*Color.*—Developing and fully expanded foliage, upper surface: 137B; venation, 144A. Developing and fully expanded foliage, lower surface: 138B; venation, 144A. Zonation pattern: Not observed.

*Petiole.*—Length: About 11.6 cm. Diameter: About 3 mm. Texture, upper and lower surfaces: Smooth, glabrous. Color, upper and lower surfaces: 144A.

Flower description:

*Flower arrangement.*—Semi-double rotate flowers arranged in rounded hemispherical umbels arising from apical leaf axils. Umbels displayed above the foliage on strong peduncles. Flowers face upright to outward. Flowers persistent. Flowers not fragrant.

*Quantity of flowers.*—Freely flowering habit; about 15 to 20 flowers per umbel.

*Flowering season.*—Year-round under greenhouse conditions. In Germany, flowering is continuous from spring throughout the summer.

*Flower longevity.*—Individual flowers last about five to seven days on the plant.

*Umbel height.*—About 5.5 cm.

*Umbel diameter.*—About 9.5 cm.

*Flower diameter.—About* 4.5 cm.

*Flower depth* (*height*).—About 1.7 cm.

*Flower buds.*—Length: About 1.7 cm. Diameter: About 9.5 mm. Shape: Ovoid. Color: 61B.

*Petals.*—Quantity per flower: About five. Length: About 2.6 cm. Width: About 2.8 cm. Shape: Obovate. Apex: Rounded. Base: Attenuate. Margin: Sinuate. Aspect: Mostly flat. Texture, upper and lower surfaces: Smooth, glabrous. Color: When opening and fully opened, upper surface: 61B. When opening and fully opened, lower surface: 61B to 61C. Venation, upper and lower surfaces: Similar to petal color.

*Petaloids.*—Quantity per flower: About one to three. Length: About 1.3 cm. Width: About 4.5 mm. Shape: Obovate. Apex: Rounded. Base: Attenuate. Margin: Sinuate. Texture, upper and lower surfaces: Smooth, glabrous. Color: When opening and fully opened, upper surface: 61B. When opening and fully opened, lower surface: 61B to 61C. Venation, upper and lower surfaces: Similar to petaloid color.

*Sepals.*—Quantity per flower: Five, arranged in a single whorl. Length: About 1 cm. Width: About 3.2 mm. Shape: Lanceolate. Apex: Apiculate. Base: Attenuate. Margin: Entire. Color, upper and lower surfaces: 144A.

*Peduncle* (*umbel stem*).—Length: About 11.75 cm. Diameter: About 2 mm to 4 mm. Strength: Moderately strong. Texture: Smooth, glabrous. Color: 144A.

*Pedicel* (*individual flower stem*).—Length: About 2.6 cm. Diameter: About 1 mm to 2 mm. Strength: Moderately strong. Texture: Pubescent. Color: 59B.

*Reproductive organs.*—Androecium: Stamen quantity per flower: About five to seven. Anther length: About 2 mm. Anther shape: Oval. Anther color: 35A. Pollen amount: Moderate. Pollen color: 28A. Gynoecium: Pistil quantity per flower: One. Pistil length: About 9 mm. Stigma shape: Parted. Stigma size: About 2 mm. Stigma color: 53B. Style length: About 2 mm. Style color: 53A. Ovary color: Close to 145D.

*Seed/fruit.*—Seed and fruit development have not been observed.

Disease/pest resistance: Plants of the new Zonal *Geranium* have not been observed to be resistant to pathogens and pests common to Zonal *Geraniums*.

Garden performance: Plants of the new Zonal *Geranium* have been observed to tolerate rain, wind, and temperatures ranging from about 5° C. to about 40° C. and have demonstrated good garden performance.

It is claimed:

1. A new and distinct Zonal *Geranium* plant named 'Dueimlyk' as illustrated and described.

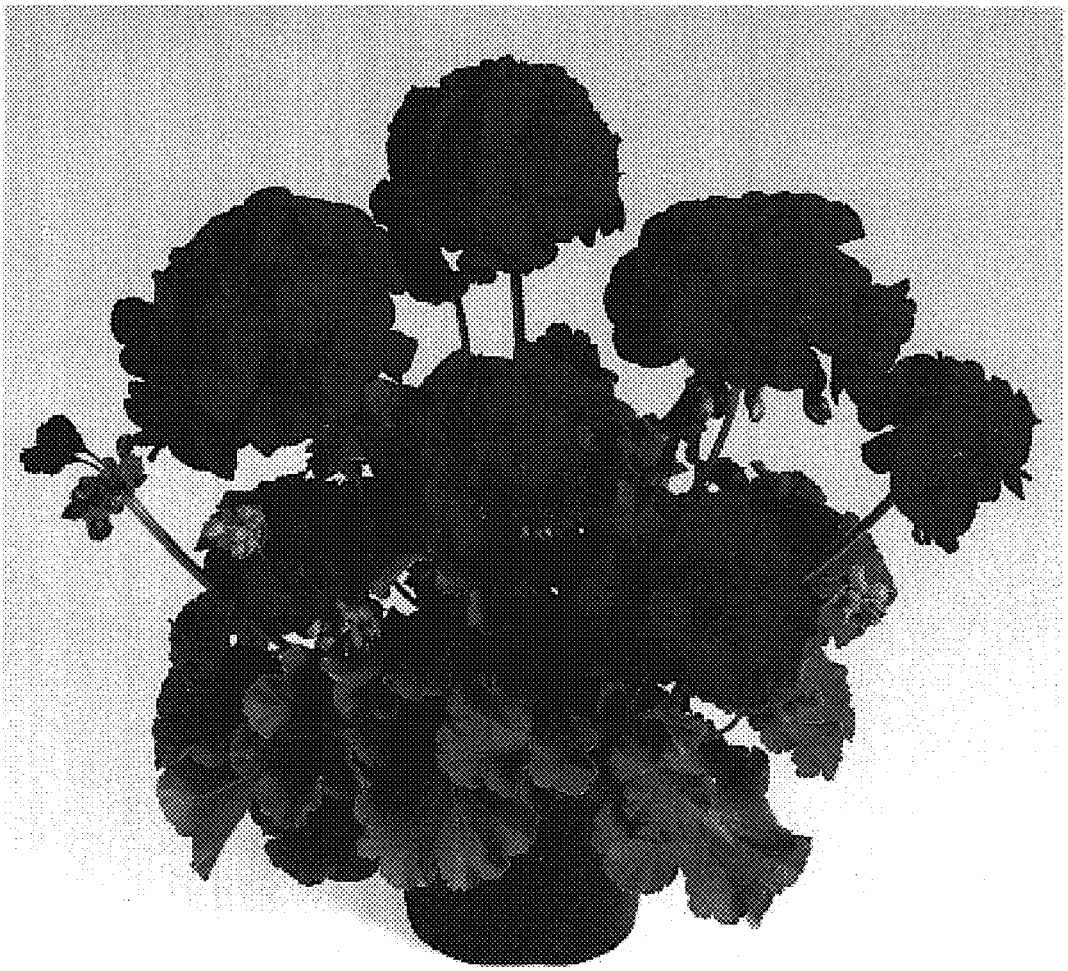

* * * * *